United States Patent
Cappelletti

(10) Patent No.: US 11,786,515 B2
(45) Date of Patent: Oct. 17, 2023

(54) ANESTHETIC MIXTURES FORMULATIONS FOR LOCAL ANESTHESIA, AT VERY LOW CONCENTRATION, TO BE USED COLD WITH SUITABLE PACKAGING

(71) Applicant: L. MOLTENI & C. DEI FRATELLI ALITTI-SOCIETA' DI ESERCIZIO S.P.A., Scandicci (IT)

(72) Inventor: Renato Cappelletti, Pozzuoli (IT)

(73) Assignee: Renato Cappelletti, Galatina (IT)

(*) Notice: Subject to any disclaimer, the term of this patent is extended or adjusted under 35 U.S.C. 154(b) by 35 days.

(21) Appl. No.: 16/967,051

(22) PCT Filed: Feb. 1, 2019

(86) PCT No.: PCT/IB2019/050817
§ 371 (c)(1),
(2) Date: Aug. 3, 2020

(87) PCT Pub. No.: WO2019/150315
PCT Pub. Date: Aug. 8, 2019

(65) Prior Publication Data
US 2021/0030729 A1 Feb. 4, 2021

(30) Foreign Application Priority Data
Feb. 1, 2018 (IT) .................. 102018000002292

(51) Int. Cl.
| | |
|---|---|
| *A61K 31/445* | (2006.01) |
| *A61K 31/137* | (2006.01) |
| *A61K 31/167* | (2006.01) |
| *A61K 31/381* | (2006.01) |
| *A61K 9/00* | (2006.01) |
| *A61K 31/195* | (2006.01) |
| *A61K 31/4748* | (2006.01) |
| *A61K 31/7036* | (2006.01) |
| *A61K 45/06* | (2006.01) |

(52) U.S. Cl.
CPC .......... *A61K 31/445* (2013.01); *A61K 31/137* (2013.01); *A61K 31/167* (2013.01); *A61K 31/381* (2013.01); *A61K 9/0019* (2013.01); *A61K 31/195* (2013.01); *A61K 31/4748* (2013.01); *A61K 31/7036* (2013.01); *A61K 45/06* (2013.01)

(58) Field of Classification Search
CPC .. A61K 31/445; A61K 31/137; A61K 31/167; A61K 31/381
See application file for complete search history.

(56) References Cited

U.S. PATENT DOCUMENTS

| | | |
|---|---|---|
| 6,329,398 B1 | 12/2001 | Zappala |
| 2014/0275170 A1 | 9/2014 | Nehleber et al. |
| 2017/0157082 A1 | 6/2017 | Poulsen et al. |

OTHER PUBLICATIONS

International Search Report and Written Opinion for corresponding Application No. PCT/IB2019/050817 (dated May 16, 2019).
Abbott et al., "The Use of a Topical Refrigerant Anesthetic to Reduce Injection Pain in Children," J. Pain Symptom Manage. 10(8):584-590 (1995).
Moya et al., Abstract of "Urticaria a Frigore: Clinical Characteristic and Diagnostic," (Jan. 2001) available at https://www.researchgate.net/publication/292871006_Urticaria_a_frigore_Clinical_characteristic_and_diagnostics.

*Primary Examiner* — Kevin E Weddington
(74) *Attorney, Agent, or Firm* — Troutman Pepper Hamilton Sanders LLP (Rochester)

(57) ABSTRACT

Subject of the present invention is a diluted anesthetic solution, to be used cold, comprising the association of two different local anesthetics, one with a short duration of action and the other with a long duration of action and optionally in association with one or more adjuvant drugs having antibiotic, antifibrinolytic or antitumor action. With this association it is possible to prolong up to 150 m' duration of action in addition to offering better management of perioperative problems both as a request for analgesic drugs for post-operative pain, but also as a support to alleviate and reduce complications in some way connected to certain surgical procedures. The invention concerns also specific packaging with specific formulations, such as to make the immediate use of the mixture itself possible for different interventions.

12 Claims, No Drawings

ANESTHETIC MIXTURES FORMULATIONS FOR LOCAL ANESTHESIA, AT VERY LOW CONCENTRATION, TO BE USED COLD WITH SUITABLE PACKAGING

This application is a national stage application under 35 U.S.C. § 371 of PCT Application No. PCT/IB2019/050817, filed Feb. 1, 2019, which claims priority benefit of Italy Application No. 102018000002292, filed Feb. 1, 2018, which are hereby incorporated by reference in their entirety.

FIELD OF THE INVENTION

The present invention relates to the field of anesthetic formulations to perform local anesthesias by infiltration; in particular, it concerns a diluted anesthetic solution, to be used cold, comprising the association of two different local anesthetics, one with a short duration of action and the other with a long duration of action and optionally further comprising other drugs in reduced dosages.

STATE OF THE ART

Local anesthesia represents a method albeit rich in prospects, at the moment still not adequately used, despite some undoubted progress made.

The current state of the art is based on the use of solutions provided of local anesthetic activities, able to reduce or abolish the pain sensitivity, or in the infiltration zone (anesthesia by infiltration), or if injected in proximity of a nerve or of specific nerve structures such as the spinal cord, throughout the area innervated by the affected nerve structure.

In summary, we can divide the methods of local anesthesia into:
a) anesthesia by infiltration, where the extent of the anesthetized area is directly dependent on the volume of the injected anesthetic solution;
b) anesthetic block, where the extent of the anesthetized area depends on the anatomical distribution of the anesthetic structure involved in the block.

The anesthesia by infiltration is the simplest to perform, but also the least used, because it can be used only on very small areas, being linked to the "volume" of the anesthetic solution to be injected, which cannot exceed a certain threshold, due to risk of serious complications of toxic type, both on the central nervous system with irritation and psychomotor agitation or convulsions up to the coma, or even alterations of the cardiac rhythm, from tachycardia to the bradycardia pushed up to the ventricular fibrillation and to the cardiac arrest.

In fact, all anesthetic solutions are burdened by a dose dependent toxicity, even if different for the various molecules, but in some way linked to the duration of their action.

Short-acting anesthetics normally have less toxicity than those to long-acting.

The toxicity is dependent on the concentration in the bloodstream of the anesthetic molecule, but also on its rate of absorption in the bloodstream, so that the infiltration of a richly vascularized area is more risky than the injection of a poorly vascularized zone.

Often a vasoconstrictor is associated to the local anesthetic, normally a sympathetic-mimetic amine, almost always in the form of adrenaline, which on one hand serves to prolong the local anesthetic duration of action, limiting the blood absorption with increasing of the local concentration, but also able to reduce its general toxicity by slowing of its absorption in the bloodstream and therefore reducing of the blood concentration.

But the vasoconstrictor is also used because, by inducing a local vasoconstriction, it reduces the bleeding of the tissues subjected to the surgical trauma and this at the end translates into something really suggestive for the optimal execution of the surgical act, determining a practically bloodless operating field.

However, also sympathomimetic amines have strict dosage limitations to be respected, because possible overdoses can induce very serious toxic reactions, such as sudden hypertensive crises or important changes in heart rhythm until to arrest.

All this ended up very much limiting the use of local anesthesia by infiltration, relegating it only to surgery on very circumscribed areas, such as small outpatient surgery or the not very invasive odontostomatology.

Local anesthetics are dosed according to well precise standards based on their dilution, which implies a constant ratio between the used volume and administered dose.

For example, for the Lidocaine hydrochloride as for the Mepivacaine hydrochloride, which from now on we will simply call Lidocaine and Mepivacaine, the optimal concentration is 1 or 2% equal to a dosage of 10 or 20 mg/ml and greater dilutions or smaller dosages result ineffective and therefore not usable.

For Lidocaine, classically the toxic doses are 4.5 mg/kg without exceeding 300 mg if used alone, for a maximum volume of 15 ml if used at 2%, while if combined with a vasoconstrictor such as adrenaline, the maximum dosage rises to 7 mg/kg and the maximum dose to 500 mg, equal to 25 ml of a 2% solution. Instead, it has been highlighted that the use of the molecule in a cold and diluted solution allows to use dosages even higher than 1 gram, without risk of toxic response, because the absorption in bloodstream results extremely slowed. Mepivacaine has similar tolerance.

Lidocaine and Mepivacaine are molecules classified as short-acting local anesthetics and therefore at lower toxicity and normally used for local infiltration anesthesia, while the anesthetics with longer duration of action such as Bupivacaine hydrochloride or Levobupivacaine hydrochloride, normally, are not used for infiltration anesthesia, for the very small usable volumes, being molecules endowed of high toxicity, with toxic dose corresponding to 2 mg/kg body, without exceeding the total 150 mg, for a maximum volume of 30 ml of the 5 mg/ml solution (0.5%).

The Articaine hydrochloride always belongs to the group of the short-acting local anesthetics. This local anesthetic is usually used almost exclusively for dentistry and used at concentrations of 4% combined with a vasoconstrictor in 1/100000 solution and the toxic dose is overlapping to that of the lidocaine and mepivacaine.

In literature (R. CAPPELLETTI: ANESTESIA PER INFILTRAZIONE CON SOLUZIONE ANESTETICA FREDDA E DILUITA; Proceedings 49th National Congress SIARTI Sorrento; Minerva Anestesiologica September 1995 Vol. 61, Suppl 2 N. 9 pag. 11) exists a very suggestive proposal to increase, up to 20 times, of the volume of local injectable anesthetic solution, without increasing of the dosage, but preserving the effectiveness.

All this is made possible simply by cooling to 4-6° C., the local anesthetic solution used for the infiltration and finally this makes it possible to perform under local anesthesia, interventions previously possible only under general anesthesia.

The above reported method is based on the injection of a local anesthetic solution diluted up to 20 times of Lidocaine or Mepivacaine, (0.1% or 1 mg/ml), +a sympathomimetic amine, in particular Adrenaline equal to 1 mg/1000 ml or 0.001 mg/ml or a dilution of 1/1000000.

This solution, absolutely ineffective, according to the current scientific canons, if used at room temperature, becomes very effective if injected after cooling to 4-6° C., allowing in this way to dispose of a "volume" of a very large anesthetic solution, able to anesthetize very large surfaces.

All this has certainly represented an enormous development potentiality of the method of anesthesia by infiltration, because with the infiltration of the diluted cold solution, in addition to a good local anesthesia, a very positive phenomenon is realized concurrently for the good result of the surgical intervention, represented by a very effective generalized vasoconstriction of the infiltrated area with significant reduction of bleeding.

Unfortunately, despite the optimal premises, the "a frigore" method set up for over 20 years, it failed to carve out an adequate space to its potential, although it has been widely publicized.

The most frequent observations, complained by surgeons who have also tried the method, put in relief the too short action duration of the mixture that, despite being about 60 m', has been considered insufficient by many, for the dead times necessary to perform the infiltration, which ended up influencing the time useful for the intervention, together with the difficulty of the mixture preparing that must be carried out extemporaneously, with risks of errors and of possible pollution during the various manipulations necessary to realize the final solution.

Wanting to give new impetus to the local anesthesia development, desirable from many points of view, it is necessary to think of researching new solutions, such as to lay the foundations for a definitive its expansion.

Aim of the present invention is the formulation of new local anesthetic mixture for infiltration always very diluted and therefore usable in large volumes, to be used cold, but able to optimize the intervention times, extending them even over 150 m', time this more than sufficient for any type of surface intervention, together with the creation of specific packaging, containing different mixtures, suitable to make the newly formulated anesthetic mixtures, immediately available on the operating field for specific interventions, without any loss of time or risk of error or contamination.

Aim of the present invention is also to provide local anesthetic mixture for infiltration which allows the execution of complex surgical treatments, offering, with respect to the execution under general anesthesia, not only an adequate duration but also a better management of perioperative problems and a reduction in post-operative complications.

SUMMARY OF THE INVENTION

Subject-matter of the present invention is an anesthetic mixture according to the present claim 1.

The advantages of an anesthetic mixture according to the present invention are mainly represented by the possible fields of application, which can be truly various, comprising all the surface intervention of both external and internal mucosal.

Thanks to the anesthetic mixture according to the present invention, in addition to a longer action duration which has surprisingly allowed the approach to even more complex interventions with a better management of perioperative problems as a request for analgesic drugs for post-operative pain, has been highlighted, but also as a support to alleviate and reduce complications in some way related to these interventions. For the external interventions, outside the peritoneal cavity, surely a separate chapter consists in the breast surgery that thanks to this method will allow to perform almost all the interventions under local anesthesia with reduction of operative risk, reduction of waiting lists and big savings on public spending; still great advantages will come for both reconstructive and aesthetic plastic surgery that thanks to the "a frigore" method, will allow, to perform almost all of the operations under local anesthesia with a practically bloodless surgical field, significant reduction of postoperative complications and certainly less surgical stress for the patient; same applies to almost all surface phlebological surgery, dermatological surgery, maxillofacial surgery, general surgery in surface interventions, orthopedic surgery where a good vasoconstriction is necessary to reduce blood loss, as well as gynecological surgery for many vaginal interventions and urological surgery for surface interventions.

For internal mucosal interventions, a separate chapter is certainly constituted by dental and maxillofacial surgery where the use of increasingly sophisticated and aggressive methods have made it difficult to manage them with the classic normothermic local anesthetic solution, because they require ever greater anesthetic volumes with risk of even serious toxic complications.

In fact, if until very recently, dentistry provided very limited interventions for extension under local anesthesia, using general anesthesia for slightly more complex interventions, today the need to can using local anesthesia methods even for complex operations is strongly felt.

The a frigore anesthesia will really mark an epochal turning for surface surgery, without forgetting the possibility of direct interventions on the gastro intestinal walls through modern endoscopic methods, as well as it is possible to intervene effectively on the vaginal mucosa and on the uterine cervix.

Subject-matter of the present invention is also a packaging system according to claim 8 and a kit according to claim 9.

DETAILED DESCRIPTION OF THE INVENTION

The cooling, as local anesthesia, had already been used in the past, with varying fortunes, for some surgical interventions, but a possible cold action on the pharmacodynamics and pharmacokinetics of a bioactive substance such as a local anesthetic or a sympathomimetic amine and also of many other drugs was never envisaged.

What is achieved by injecting a diluted and cooled anesthetic solution has never been the subject of a targeted scientific investigation, despite the evidence of a result undoubtedly spectacular and in some ways outside the current rational capacity to grasp the phenomenon.

Cold has always been used to reduce pain sensitivity, but the mechanism that is established with the infiltration of a cold and diluted anesthetic solution is probably much more complex involving a response to the chemical stimulation of the anesthetic solution+a biological response to physical cold stimulation.

In all likelihood it is precisely the biological response to physical cold stimulation which determines the interference with the normal pharmacokinetics and pharmacodynamics of the diluted anesthetic solution, enhancing its pharmacological characteristics.

In reality, with the intratissutal injection of a cold solution (4-6° C.) a certain thermal gradient is determined between the injected solution and the treated area which is directly proportional to the temperature of the injected solution, to the injected volume and inversely proportional to the infiltrated surface.

In fact, the effectiveness of the solution is directly dependent on the thermal gradient that can produce.

Consequently, where it is possible to inject large volumes of cold solution, a large thermal gradient will be obtained, determined by the ratio between the volume of injected solution at a certain temperature (4-6° C.) and the infiltrated area with a temperature of about 37° C. and consequently, in these areas the maximum effectiveness of the cold solution will be obtained, which can be used at the maximum dilution.

Where instead it is not possible to inject large volumes of solutions for anatomical situations or for the smallness of the area to be treated, it will be determined inevitably a lower thermal gradient and consequently a lower efficacy of the solution which, to obtain optimal results, it will have to be slightly more concentrated.

The interference of the thermal gradient on the pharmacodynamics and pharmacokinetics of a bioactive substance it not concerns only local anesthetics or sympathomimetic amines but involves many drugs that can be used at really low doses thanks to this method.

In the so-called warm-blooded organisms exists a very sophisticated endothermic thermoregulation system that involves many extremely sophisticated systems, with activation of complex neuroendocrine responses, in response to even minimal variations in body temperature.

Greater is the thermal gradient created in a certain area, greater will be the neuroendocrine response triggered by this stimulation.

Starting from these assumptions, it was proposed an innovative anesthetic mixture able to make a leap forward expected for years in the field of infiltration anesthesia, compared to the current background, such as to determine a probable revolution in current techniques of local anesthesia.

Subject of the present invention is an anesthetic mixture which, although very diluted, is able to guarantee a good anesthesia, for a suitable time, together with a good vasoconstrictive action to minimize local bleeding without risk of generalized alterations, but also usable for optimal efficacy as postoperative analgesia, and for the better management of many intra and perioperative problems, enclosing in a single mixture different products, at very reduced concentrations, able to integrate in order to guarantee a better execution of the surgical action.

To be able to achieve the objectives of the invention, the association of two different local anesthetics was used, endowed of different duration of action, such as Lidocaine hydrochloride, Mepivacaine hydrochloride or Articaine hydrochloride, labeled as short-acting anesthetics, associated to Bupivacaine hydrochloride or Levobupivacaine hydrochloride defined as long-acting anesthetics.

The first, with a short-acting, being able to guarantee a very good on set, with the establishment of a good anesthesia in very quick times (1-3 m'), while the second, with a long-acting, having to contribute to prolong anesthetic action even over 150 m'.

The set of the two different molecules integrates perfectly, allowing on the one hand an anesthetic effect with a very rapid onset and on the other, prolonging the effect for suitable times for safe use for interventions also of a certain complexity.

Obviously, the possibility of association between short-acting anesthetics and long-acting anesthetics is extremely rich, but the basic concept is comparable for all: associating the two types of anesthetics overlapping results are obtained that not concern only an extension of the anesthetic properties of the mixture, but also a subsequent long analgesic action.

The basic formulations shown below are only an example of the possible associations today achievable between short- and long-acting anesthetics, but the results are always overlapping.

Subject of the present invention is therefore the formulation of different anesthetic mixtures, always very diluted, with respect to the formulations of the official pharmacopoeia, to be used after cooling up to 4-6° C., made up of the association of a short-acting local anesthetic+a long-acting local anesthetic.

Optionally, an anesthetic mixture according to the present invention may further comprise one or more other adjuvant drugs for carrying out a given surgical intervention. For other drugs, are meant active principles with non-anesthetic action and preferably chosen from antibiotics, anticancer, antifibrinolytics. Such drugs can be used in dosages lower than $1/10$ of the standard pharmacopoeia dose. In some cases it can be verified, through appropriate clinical trials, that the minimum effective dose of these adjuvant drugs in the mixtures according to the invention may be even lower than $1/50$ of the standard pharmacopoeia dose.

In relation to the specificity of the use and therefore of the type of intervention to be carried out, we initially envisaged the realization of three different types of solutions that will be inevitably linked also to specific packaging, obviously without excluding the possibility of different formulations, specific for different surgical interventions.

A more diluted anesthetic mixture that we will call "mixture A", a slightly more concentrated anesthetic mixture that we will call "mixture B" and a specific anesthetic mixture, for dentistry, "mixture C", that still diluted and to be used cold, presents a mixture a little more concentrated compared to the previous ones, packaged in standard 1.8 ml cartridges, to be used with carpule syringes, specific for intraoral anesthesia.

The type "A" solution will be so set up for preparing 1000 ml:
 Lidocaine or Mepivacaine one gram, achieving a final solution at 0.1% (1 mg/ml);
 Bupivacaine or Levobupivacaine 100 mg, achieving a final solution at 0.01% (0.1 mg/ml);
 Adrenaline one milligram, achieving a final solution of $1/1000000$ (0.001 mg/ml)
 Solution, enough for one liter, whether isotonic, whether hypotonic or hypertonic;

For the type "B" solution, the preparation of 1000 ml will be so composed:
 Lidocaine or Mepivacaine 1.5 grams, achieving a final solution at 0.15% (1.5 mg/ml);
 Bupivacaine or Levobupivacaine 150 mg, achieving a final solution at 0.015% (0.15 mg/ml);
 Adrenaline 1.5 milligrams, achieving a final solution of $1/666666$ (0.0015 mg/ml);
 solution, enough for one liter, whether isotonic, whether hypotonic or hypertonic.

For the type "C" solution, the preparation of 1000 ml will be so composed:

Articaine hydrochloride 5 grams, achieving a final solution at 0.5% (5 mg/ml);

Bupivacaine hydrochloride or levobupivacaine hydrochloride 500 mg achieving a final solution at 0.05% (0.5 mg/ml);

Adrenaline 4 milligram, achieving a final solution of 1/250000 (0.004 mg/ml);

Solution, enough for one liter, whether isotonic, whether hypotonic or hypertonic.

The mixture "A" will be used to anaesthetize large surfaces, while the mixture "B" will be used for minor surfaces, and the "C" mixture using an ad hoc packaging, will be used specifically for the oral cavity.

Each of the above-mentioned mixtures may further comprise an antibiotic (e.g. gentamicin 0.08 mg/ml), or an antifibrinolytic (Tranexamic acid 1 mg/ml) or an anticancer (e.g., vincristine 0.1 µg/ml) or mixtures thereof.

Inevitably, each mixture will adopt a specific packaging:
the "A" mixture will have a packaging that will use higher volumes, equal to 250-500 ml;
the "B" mixture will have a packaging that will use smaller volumes, equal to 50-100 ml;
the mixture "C" will have a specific packaging in cartridges of 1.8 ml.

In addition to different volumes, the packaging of the above described solutions will adopt a series of precautions so as making optimal the use of the individual solutions, having the solutions described above be subjected to cooling by common refrigerators and once extracted from the fridge to store for as long as possible the optimal use temperature.

For this purpose it is necessary to provide a suitable packaging, so that the solutions adopted must be considered an integral part of the present instance.

Moreover, since the solution packaged in its specific packaging will be usable directly on the operating field, the packaging must meet specific requirements:

The basic packaging for the type "A" and "B" solutions is consisting of a three envelopes system, of which the non-sterile external one will allow its storage and its use in a normal fridge. This external, we repeat, non-sterile, with flip-off opening, will allow access to the sterile inner container, consisting of an isothermal cover made of reflecting material with the task of preserving the optimal temperature of the content for a longer time, once extracted from the fridge, but also to made up protection from light during the normal storage of the bags. In fact, the light could with time alter some of the mixture components. Inside the isothermal cover will be contained the real bag with the anesthetic mixture inside;

The container of the mixture must be in non-rigid material, with an access system to its content adapted to allow the drawal of the content without allowing air to enter inside, to balance the external pressure, this to avoid risks of environmental contamination.

The internal sterile container is equipped, in an area left exposed, also with a thermometric strip calibrated at 4-8° C., to check its optimal temperature.

Each bag is integrated of specific kit, also this having double envelope, an external non sterile flip-off openable having inside the container of the sterile kit for the drawal of anesthetic solution directly on the operating table, consisting of a flow tube without air valve, adapted to use the access system of the anesthetic solution container, equipped with an end tap, luer lock type, to which hook a syringe or other sampling system, in order to perform the injection of the solution always without contact with the ambient air.

A separate chapter must be made for the packaging of the "C" solution, concerning the packaging in cartridges. The cold management of the cartridges certainly represents an important problem for the small volume and the large surface of thermal exchange between the environment and the solution, such to allow the cold solution to quickly heat. To allow cooling and cold storage of the cartridges, once extracted from the fridge, they are placed in a polystyrene isothermal container, with specific housings for each single cartridge, in a variable number from 3 to 10, individually sealed and labeled with appropriate isothermal flip-off coverage.

In addition, to better preserve the thermal stability of the cartridges, they can be covered with a reflective paint.

In the so-called complex interventions the problems to be managed are often multifactorial and the anesthetic mixtures subject of the present invention, used as a single anesthetic or in some cases as supplementary anesthesia, have proved to can allowing the carrying out of notoriously complex interventions (which require surgery times of even over 150 m') and also allowing surprisingly to significantly improve the management of perioperative problems and reduce the onset of complications related to certain surgical interventions.

For example the surgical treatment of the progenism is performed under general anesthesia with endotracheal intubation and it forces, due to the important edematogenic component of the treated muscles, to the persistence of postoperative endotracheal intubation for 24-36 hours with the need for intensive postoperative assistance concomitant with the administration of analgesics in 24-36 hours post-surgery. Furthermore, since the risk of infection in the oral cavity is a frequent event, it forces to prolong antibiotic therapies.

Surgical treatment of the progenism performed under general anesthesia with endotracheal intubation, with a supplementary a frigore infiltration of the masseter muscles with an anesthetic mixture according to the present invention (200-300 ml of anaesthetic solution of type "A" cooled to 4-6° C.) with the addition also of antibiotic (gentamicin 0.08 mg/ml for a total of 16-24 mg gentamicin administered corresponding to about 1/10 of the pharmacopoeia dose) it has allowed to significantly reduce the edematogenic component of the treated muscles to the point of allowing extubation of the patients already a few hours after surgery without the need for intensive post-operative care and has also significantly allowed to reduce the administration of analgesics in the 24-36 hours post-operatively, also reducing the onset of post-surgery infectious complications.

Thanks to this experimentation, the use of the antibiotic in association with the anesthetic mixture it has by now become habitual practice, allowing thanks to the thermal gradient to achieve locally an excellent anti-infective prevention with truly reduced antibiotic dosages.

In the surgical treatment of the marginal tumor of the tongue in which it is necessary to perform a hemiglossectomy that expects, when performed under general anesthesia only, the preparation to the neck of the carotid artery and of the lingual artery to protect against possible bleeding damage.

The surgical treatment of the marginal tumor of the tongue performed instead by local anesthesia by a frigore infiltration with an anesthetic mixture according to the present invention (i.e. 100-150 ml of anaesthetic solution of type "A" cooled to 4-6° C.) allows to perform the intervention practically in a bloodless field, avoiding the preparation to the neck of the carotid artery and lingual artery. Surprisingly with a such anesthetic procedure it was possible verifying an excellent post-surgical recovery of the patients who are able to speak only a few hours after the surgery. For such a surgery the anesthetic mixture subject of the present invention has been added also with Tranexamic acid (1 mg/ml for a total of 100-150 mg of Tranexamic acid administered corresponding to about 1/10 of the pharmacopoeia dose) and the results have been surprising enough to push to use routinely the supplementation with mini doses of antifibrinolytics in most of the surgery at risk of bleeding.

An anesthetic mixture according to the present invention (for example 400-500 ml of type "A" anesthetic solution cooled to 4-6° C.) added with micro doses of antitumor chemotherapeutics (e.g. vincristine sulphate 0.1 μg/ml for a maximum dosage of 0.05 mg corresponding to less than 1/50 of the pharmacopoeia dose), such as to allow its use for local way, will allow the surgical treatment (mastectomy) of breast tumors allowing to reduce, thanks to the local vasoconstriction, the risk of intra-surgery tumor dissemination and also performing, thanks to the presence of the antitumoral, a possible localized antitumor therapy.

In hip arthroprothesis the infiltration of an anesthetic mixture according to the present invention (e.g. 400-500 ml of anaesthetic solution of type "A" cooled to 4-6° C.) added with antibiotic (gentamicin 0.08 mg/ml) and antifibrinolytic (Tranexamic Acid 1 mg/ml) in the area of surgical aggression, determines drastic reduction of both intra and post-surgical bleeding, without need anymore of having to resort to transfusions, and allows a reduction in the post-surgery antalgic therapy request, in addition to considerably reducing the risk of local infectious complications.

The invention claimed is:

1. A local anesthetic mixture for infiltration a frigore; comprising:
   at least one short-acting local anesthetic in concentration 1-5 mg/ml;
   at least one long-acting local anesthetic in concentration 0.1-0.5 mg/ml;
   at least one sympathomimetic amine in concentration 0.001-0.004 mg/ml;
   optionally at least one further active substance adjuvant having a non-anesthetic action in a maximum dosage equal to 1/10 compared to the standard pharmacopoeia dose;
   isotonic, hypotonic or hypertonic solution q.s. to obtain the aforementioned concentrations;
   said mixture to be administered cooled to a temperature of 4-8° C.

2. The anesthetic mixture according to claim 1, in which said further non-anesthetic active substance is selected from the group consisting of antibiotics, anticancer, antifibrinolytics.

3. The local anesthetic mixture according to claim 1, wherein
   the short-acting anesthetic is selected from the group consisting of Lidocaine hydrochloride, Mepivacaine hydrochloride and Articaine hydrochloride;
   the long-acting anesthetic is selected from the group consisting of Bupivacaine hydrochloride and Levobupivacaine hydrochloride;
   the sympathomimetic amine is adrenaline.

4. The anesthetic mixture according to claim 1 comprising:
   Lidocaine hydrochloride or Mepivacaine hydrochloride 1 mg/ml;
   Bupivacaine hydrochloride or Levobupivacaine hydrochloride 0.1 mg/ml;
   Adrenaline 0.001 mg/ml.

5. The anesthetic mixture according to claim 1 comprising:
   Lidocaine hydrochloride or Mepivacaine hydrochloride 1.5 mg/ml;
   Bupivacaine hydrochloride or Levobupivacaine hydrochloride 0.15 mg/ml;
   Adrenaline 0.0015 mg/ml.

6. The anesthetic mixture according to claim 1, comprising:
   Articaine hydrochloride 5 mg/ml;
   Bupivacaine hydrochloride or Levobupivacaine hydrochloride 0.5 mg/ml;
   Adrenaline 0.004 mg/ml.

7. The anesthetic mixture according to claim 4, further comprising gentamicin 0.08 mg/ml, or Tranexamic acid 1 mg/ml or vincristine 0.1 m/ml or mixtures thereof.

8. A method of local anesthesia by infiltration with frigore in which the anesthetic mixture according to claim 1 is administered to a subject in need thereof cold at a temperature of 4-8° C. so as to obtain a thermal gradient in the infiltrated tissue.

9. A packaging system of the anesthetic mixture according to claim 1, comprising a sterile container coated by an isothermal material, said container equipped with a disposable perforable cap and equipped with self-adhesive thermometric label, in such a way as to be able to verify that the mixture at the moment of its use is actually cooled to the optimum temperature of use, which is 4-8° C.

10. A kit comprising the anesthetic mixture packaged in a packaging system according to claim 9 and further comprising a sterile kit for picking up the anesthetic solution directly on the operating table, consisting of a flow tube without air valve, suitable to use the access system of the anesthetic solution container, equipped with an end tap, luer lock type, to which hook a syringe or other sampling system, in order to perform the injection of the solution always without that this never contacts the ambient air.

11. The anesthetic mixture according to claim 5, further comprising gentamicin 0.08 mg/ml, Tranexamic acid 1 mg/ml, vincristine 0.1 μg/ml, or mixtures thereof.

12. The anesthetic mixture according to claim 6, further comprising gentamicin 0.08 mg/ml, Tranexamic acid 1 mg/ml, vincristine 0.1 μg/ml, or mixtures thereof.

* * * * *